(12) United States Patent
Bianchi et al.

(10) Patent No.: US 12,053,358 B2
(45) Date of Patent: *Aug. 6, 2024

(54) ABSORBENT CORE COMPRISING A HIGH LOFT CENTRAL LAYER AND CHANNELS

(71) Applicant: The Procter & Gamble Company, Cincinnati, OH (US)

(72) Inventors: Ernesto Gabriel Bianchi, Oberursel (DE); Bruno Johannes Ehrnsperger, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/392,615

(22) Filed: Aug. 3, 2021

(65) Prior Publication Data

US 2021/0361497 A1 Nov. 25, 2021

Related U.S. Application Data

(63) Continuation of application No. 14/965,920, filed on Dec. 11, 2015, now Pat. No. 11,110,014.

(30) Foreign Application Priority Data

Dec. 23, 2014 (EP) ..................................... 14200134

(51) Int. Cl.
*A61F 13/534* (2006.01)
*A61F 13/15* (2006.01)
(Continued)

(52) U.S. Cl.
CPC ...... *A61F 13/534* (2013.01); *A61F 13/15658* (2013.01); *A61F 13/15699* (2013.01);
(Continued)

(58) Field of Classification Search
CPC .......... A61F 13/15658; A61F 13/15699; A61F 13/5323; A61F 13/534; A61F 2013/530489; A61F 2013/5349
See application file for complete search history.

(56) References Cited

U.S. PATENT DOCUMENTS

| | | | |
|---|---|---|---|
| 5,429,788 A | 7/1995 | Ribble et al. | |
| 5,807,364 A * | 9/1998 | Hansen | D06M 13/256 442/164 |

(Continued)

FOREIGN PATENT DOCUMENTS

| | | |
|---|---|---|
| CN | 1206341 A | 1/1999 |
| CN | 1750801 A | 3/2006 |

(Continued)

OTHER PUBLICATIONS

All Office Actions; U.S. Appl. No. 14/965,920, filed Dec. 11, 2015.
(Continued)

*Primary Examiner* — Michele Kidwell
(74) *Attorney, Agent, or Firm* — Daniel S. Albrecht; Sarah M. DeCristofaro

(57) ABSTRACT

An absorbent core for use in an absorbent article, the absorbent core extending in a transversal direction and a longitudinal direction. The absorbent core includes a fluid-permeable top layer, a bottom layer, and a central layer between the top layer and the bottom layer. The central layer may be a high loft fibrous nonwoven layer, in particular having a density of less than about 0.200 g/cc, measured at a pressure of 4.14 kPa. Superabsorbent polymer particles may be blended with the fibers of the central layer, except for one or more longitudinally-extending channels substantially free of superabsorbent polymer particles.

20 Claims, 11 Drawing Sheets

(51) Int. Cl.
*A61F 13/53* (2006.01)
*A61F 13/532* (2006.01)

(52) U.S. Cl.
CPC .................... *A61F 13/5323* (2013.01); *A61F 2013/530489* (2013.01); *A61F 2013/5349* (2013.01)

(56) References Cited

U.S. PATENT DOCUMENTS

| | | | |
|---|---|---|---|
| 6,790,798 | B1 | 9/2004 | Suzuki |
| 7,744,576 | B2 | 6/2010 | Busam |
| 10,028,867 | B2 | 7/2018 | Ehrnsperger et al. |
| 10,071,002 | B2 | 9/2018 | Bianchi et al. |
| 11,110,014 | B2 * | 9/2021 | Bianchi ............ A61F 13/15699 |
| 2003/0149413 | A1 | 8/2003 | Mehawej |
| 2006/0024433 | A1 | 2/2006 | Blessing |
| 2006/0206091 | A1 | 9/2006 | Cole et al. |
| 2006/0253092 | A1 | 11/2006 | Ponomarenko et al. |
| 2007/0191798 | A1 | 8/2007 | Glaug et al. |
| 2007/0219521 | A1 | 9/2007 | Hird |
| 2008/0312618 | A1 | 12/2008 | Hundorf et al. |
| 2009/0053521 | A1 | 2/2009 | Goda et al. |
| 2010/0051166 | A1 | 3/2010 | Hundorf |
| 2010/0062165 | A1 | 3/2010 | Suzuki et al. |
| 2010/0099781 | A1 | 4/2010 | Tian et al. |
| 2011/0250413 | A1 | 10/2011 | Lu |
| 2011/0268932 | A1 | 11/2011 | Catalan |
| 2011/0319848 | A1 | 12/2011 | Mckiernan |
| 2012/0316526 | A1 | 12/2012 | Rosati et al. |
| 2012/0316529 | A1 | 12/2012 | Kreuzer et al. |
| 2012/0318046 | A1 | 12/2012 | Ehrnsperger et al. |
| 2014/0005622 | A1 | 1/2014 | Wirtz |
| 2014/0005623 | A1 | 1/2014 | Wirtz et al. |
| 2014/0249497 | A1 | 9/2014 | Bissah et al. |
| 2014/0324008 | A1 | 10/2014 | Hundorf et al. |

FOREIGN PATENT DOCUMENTS

| | | |
|---|---|---|
| CN | 101797201 A | 8/2010 |
| CN | 103202745 A | 7/2013 |
| EP | 1078618 A2 | 2/2001 |
| EP | 1722020 A1 | 11/2006 |
| EP | 0947549 B1 | 11/2011 |
| EP | 2535027 A1 | 12/2012 |
| EP | 2617401 A2 | 7/2013 |
| EP | 2679209 A1 | 1/2014 |
| JP | S62170246 A | 7/1987 |
| JP | H09156012 A | 6/1997 |
| JP | 2002113800 A | 4/2002 |
| JP | 2004275352 A | 10/2004 |
| JP | 2008237450 A | 10/2008 |
| JP | 4246413 B2 | 1/2009 |
| WO | 0121122 A1 | 3/2001 |
| WO | 2006098946 A1 | 9/2006 |
| WO | 2012170798 A1 | 12/2012 |

OTHER PUBLICATIONS

Third Party Opposition for S14200134.6 dated Apr. 26, 2019, 12 pages.
PCT Suppl. Search Report and Written Opinion for PCT/US2015/065801 dated Feb. 5, 2016, 12 pages.
Computer printout of OJI Konocloth Co., Ltd., Sep. 20, 2019 "What are Nonwoven Fabrics?" https://www.kinocloth.co.jp/english/what_is_nonwoven/, pp. 2.
Edana, "evidence of common general knowledge", Published on Mar. 23, 2013; p. 04.
Patrick Barge, "Nonwoven congress Fighting Leakage In Thin Diapers", dated Feb. 13-16, 1996, pp. 05.

* cited by examiner

ABSORBENT CORE COMPRISING A HIGH LOFT CENTRAL LAYER AND CHANNELS

FIELD

The invention relates to absorbent cores for use in personal hygiene absorbent articles. The absorbent cores may be in particular be used in baby diapers or training pants.

BACKGROUND

Absorbent articles for personal hygiene such as disposable baby diapers, training pants for toddlers or adult incontinence undergarments, are designed to absorb and contain body exudates, in particular urine. These absorbent articles comprise several layers providing different functions, typically including a topsheet, a backsheet and in-between an absorbent core, among other layers.

The absorbent core should be able to absorb and retain the exudates for a prolonged amount of time, for example overnight for a diaper, minimize re-wet to keep the wearer dry, and avoid soiling of clothes or bed sheets. The majority of currently marketed absorbent cores comprise as absorbent material a blend of comminuted wood pulp cellulose fibers with superabsorbent polymers (SAP) particles, also called absorbent gelling materials (AGM).

Absorbent cores without cellulose fibers (also called "airfelt-free" cores) have also been proposed. The SAP particles may be for example enclosed within discrete pockets formed between two substrates, or the SAP particles may be adhesively attached to a core wrap by an adhesive. Absorbent structures that comprise superabsorbent polymers, optionally a cellulosic material, and at least a pair of substantially longitudinally extending absorbent material free zones that can form channels as the absorbent structure absorb a fluid have also been disclosed. Other types of airfelt-free cores have been disclosed. Typically airfelt-free cores require high permeability SAP to perform optimally because there are no cellulose fibers to draw the fluid by capillarity within the core. High permeability SAP may however have a lower absorbent capacity and be more costly than conventional SAP used in airfelt core.

While the previously proposed absorbent cores can provide good absorbency capacity, there is a continuous need to improve the properties of cores in a cost effective manner. In particular there is a continuous need to improve wearing comfort, increase production speed and reduce raw material usage while keeping optimal fluid management properties.

SUMMARY

The present invention is directed to an absorbent core extending in a transversal direction and a longitudinal direction, and comprising a fluid-permeable top layer, a bottom layer, and a central layer sandwiched between the top layer and the bottom layer. The central layer is a high loft fibrous nonwoven layer having a front edge, a back edge and two longitudinally extending side edges. The central layer comprises superabsorbent polymer particles blended with the fibers of the central layer and, as seen from above the plane formed by the transversal and longitudinal directions, one, two or more longitudinally-extending channel zones (herein referred to as "channels"), which are substantially free of superabsorbent polymer particles. The channels may be spaced away from the two longitudinally extending side edges.

The high loft central layer may be free of cellulose fibers, and more generally the whole of the absorbent core may be free of cellulose fibers. The absorbent cores can however use SAP materials similar to those used in cellulose fibers containing cores. In particular the SAP particles used may have a permeability at equilibrium expressed as UPM (Urine Permeability Measurement) value of less than 30, in particular less than 20, or less than 15, or less than 10 UPM units, where 1 UPM unit is $1\times10^{-7}$ $(cm^3 \cdot s)/g$. Such low UPM SAP are typically used in conventional airfelt containing absorbent cores. The UPM value is measured according to the UPM Test method set out in herein-below in the "test procedure" section. The UPM Test method measures the flow resistance of a pre-swollen layer of superabsorbent polymer particles, i.e. the flow resistance is measured at equilibrium. Therefore, such SAP particles having a low UPM value exhibit a low permeability when a significant volume of the absorbent article is already wetted by the liquid exudates. These SAP having a low UPM value are typically cheaper than higher UPM material, but may be the source of leakage if a large amount of fluid such as urine is to be absorbed in a short time in airfelt free cores. In the present invention, the high loft of the central layer and the channels cooperate to provide fluid passages that more efficiently use these SAP having a low UPM values. An insulting fluid may be more efficiently directed through the channels inside the core, as well as being distributed over the length of the channels to larger areas of the core, while the void areas of the high loft layer also provide for an improved fluid passage. When the channels are spaced away from the longitudinally extending side edges, this further reduces the risk of side leakage.

In addition, as the SAP swells in the areas outside the channels, the later will form three-dimensional depressions that, particularly in the crotch area, may provide zones which can be more easily compressed in cross-direction by the thighs of the users. In other words, the channels may become bending lines for enhanced fit and comfort when the SAP has swollen. The top, central and bottom layers may be attached to each other in the channel zones for example by gluing, mechanical bonding, ultrasonic bonding or heat bonding in the channels to create more permanent three-dimensional depressions when the SAP swells.

The top layer and the bottom layer may each be a nonwoven material. Low basis weight paper, which is readily available and a relatively cheap substrate, could also be used as top layer and/or bottom layer. The absorbent core may also comprise a wrapping layer that completely covers the bottom layer and forms a C-wrap around the longitudinally extending side edges of the central layer to at least partially cover the top layer. The C-wrap may be formed in the other direction too, i.e. completely covering the top layer and at least partially covering the bottom layer. A wrapping layer can provide an improved control of the SAP thus preventing losses on the side edges of the core.

Each of the channels may be completely surrounded by the rest of the central layer comprising SAP particles, or the channels may extend from the front edge to back edge of the central layer. The first configuration provides additional benefits in terms of reduced leakages towards the front and back end of the core. On the other hand, the front end and back end are typically relatively spaced away from the site of urine deposition. The second configuration may thus be in general acceptable, and may be easier to make, as it can be made for example with a static shielding frame, as will be discussed further below.

The absorbent cores may comprise a dual layer construction comprising a first central high loft layer and a second central high loft layer. This construction may provide additional benefit for example in terms of SAP immobilization because the SAP particles may be sandwiched between these two layers. The present invention also relates to processes for making the absorbent cores of the invention. Various processes may be used, some of which are further disclosed below and in the claims. These and other optional features of the invention will be described in the following description.

DETAILED DESCRIPTION

Introduction

Figure 1:
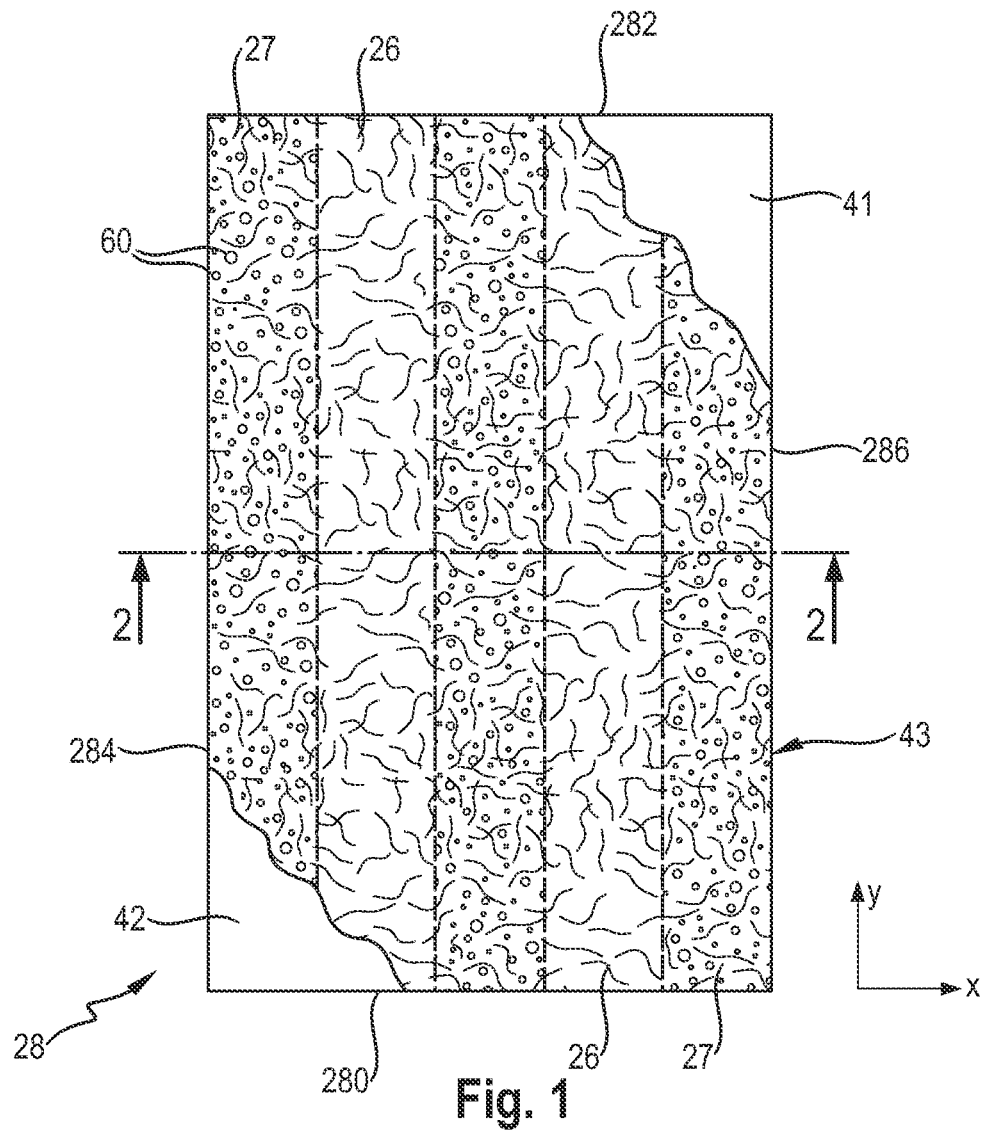
FIG. 1 shows a top view of an exemplary absorbent core with the top and central layers partially removed and channels extending along the full length of the core.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

As used herein, the terms "nonwoven layer" or "nonwoven web" are used in the general meaning of a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

General Description of the Absorbent Core

As used herein, the term "absorbent core" refers to an individual component, which is placed, or is intended to be placed, within an absorbent article and which comprises an absorbent material. The absorbent core is typically the component of an absorbent article that has the most absorbent capacity of all the components of the absorbent article and which comprises all, or at least the majority of, superabsorbent polymer (herein referred to as "SAP") particles. The terms "absorbent core" and "core" are herein used interchangeably.

The absorbent cores of the invention are substantially planar. By substantially planar, it is meant that the absorbent core can be laid flat on a planar surface. The absorbent cores may also be typically thin and conformable, so that they can also be laid on a curved surface for example a drum during the making process, or stored and handled as a continuous roll of stock material comprising a plurality of cores before being converted into an absorbent article.

Figure 6:
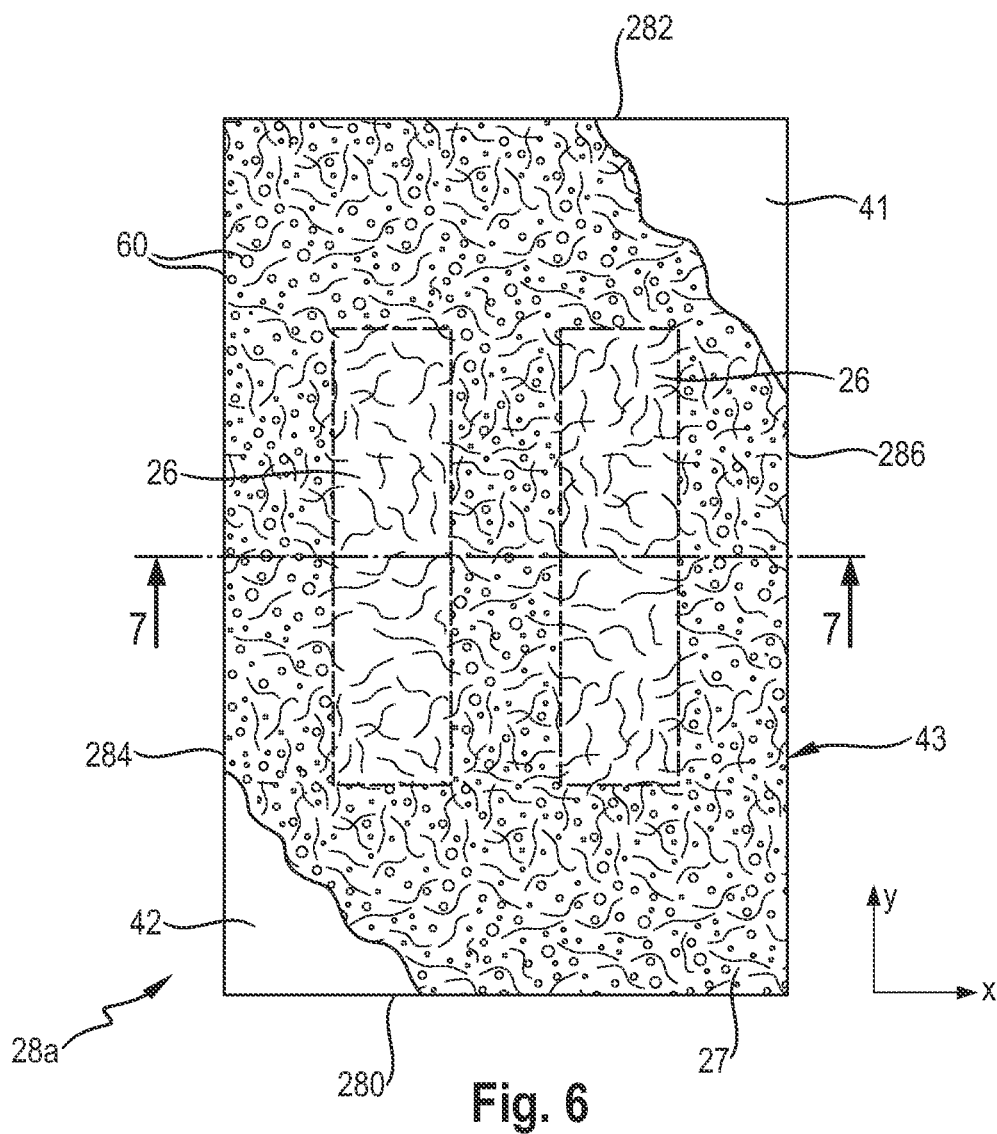
FIG. 6 shows a top view of an alternative absorbent core wherein the channels are completely surrounded by a SAP containing zone.
Figure 7:
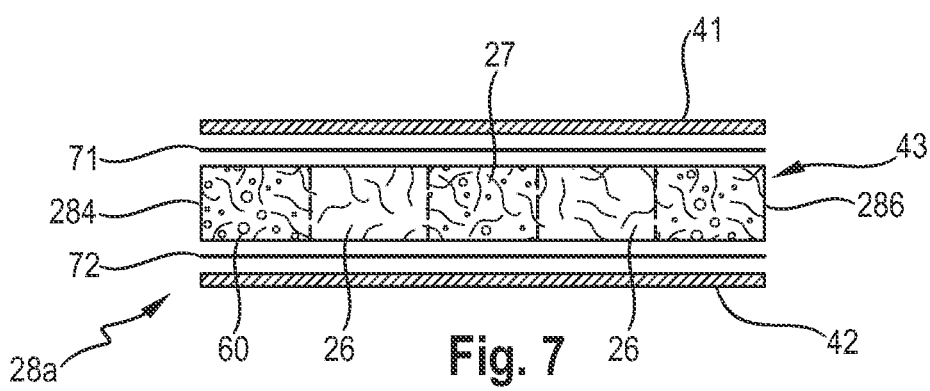
FIG. 7 shows a cross-section of the core of FIG. 6.

For ease of discussion, the exemplarily absorbent cores of FIG. 1 and FIG. 6 are represented in a flat state. The absorbent core is relatively thin relative to its other dimensions in the transversal direction (x) and the longitudinal direction (y). Unless otherwise indicated, dimensions and areas disclosed herein apply to the core in this flat-out configuration. The absorbent article may be notionally divided by a longitudinal axis (also called longitudinal centerline, not shown in the Figures) extending from the front edge to the back edge of the core and dividing the core in two substantially symmetrical halves relative to this axis, when the core is placed flat and viewed from above as in FIG. 1 for example.

For ease of discussion, the absorbent cores, articles and processes of the invention will be discussed with reference to the Figures and the numerals referred to in these Figures; however these are not intended to limit the scope of the claims unless specifically indicated.

Central Layer

Figure 2:
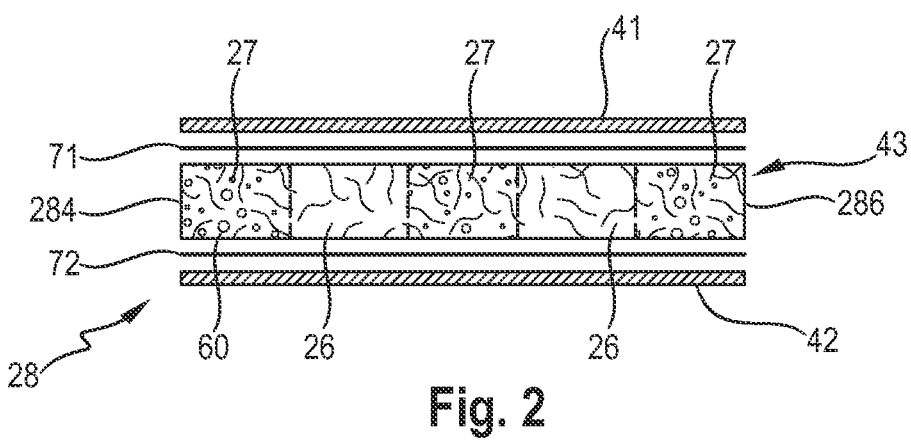
FIG. 2 shows a cross-sectional view of the absorbent core of FIG. 1.

The absorbent cores of the invention comprise a central layer 43, as first illustrated in FIGS. 1-2. The central layer 43 is a high loft nonwoven fibrous layer. The term "high loft"

refers to low density bulky fabrics, as compared to flat, paper-like fabrics. High loft webs are characterized by a relatively low density. This means that there is a relatively high amount of void space between the fibers in which the superabsorbent particles can be blended in. The high loft nonwoven fibrous layer (without the superabsorbent material) of the invention may typically have a density below 0.200 g/cc, in particular ranging from 0.015 g/cc to 0.150 g/cc, in particular from 0.030 g/cc to 0.100 g/cc, for example 0.065 g/cc. The density can be calculated by dividing the basis weight of the high loft layer by its thickness measured at a pressure of 4.14 kPa (see the method details further below in the "test procedure" section).

The high loft nonwoven layer may advantageously be a spunmelt nonwoven. Spunmelt is a generic term describing the manufacturing of nonwoven webs directly from thermoplastic polymers. It encompasses 2 processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web. Illustrations of these processes are for example provided on the Edana website: http://www.edana.org/discover-nonwovens/how-they're-made/formation.

The fibers forming the central layer may be made partially or entirely of a relatively resilient synthetic fibers, in particular polypropylene (PP), polyamide (PA, such as nylons) or polyethylene terephthalate (PET) fibers. The diameter of the fibers may for example range from 0.01 mm to 0.50 mm.

Figure 10:
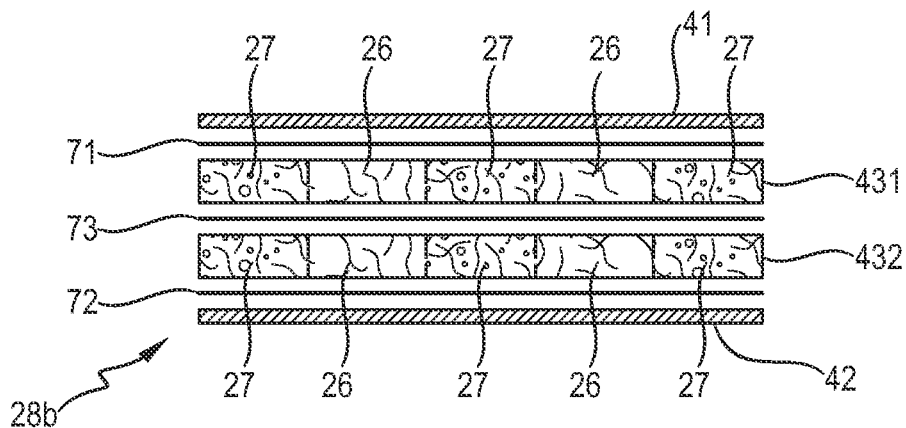
FIG. 10 shows a cross-section view of an alternative absorbent core comprising two central high loft nonwovens.

Typically the central layer will be homogenous in both transversal direction and longitudinal direction, especially regarding its thickness, basis weight and density. The high loft nonwoven layer may in particular have a thickness ranging from 0.30 mm to 2.00 mm, for example 1.0 mm as measured at a pressure of 4.14 kPa (according to the test method described further below). The basis weight of the high loft central layer may for example range from 15 gsm to 500 gsm, in particular from 30 gsm to 200 gsm, for example 64 gsm. The values indicated herein for the central layer are considered for the high loft nonwoven material taken in isolation, that is before the SAP particles have been blended between the fibers of an adhesive applied to it. When the absorbent core comprises two or more high loft central layers, as will be discussed further below, these ranges for the thickness and basis weight may be the same for each layer, or may be divided by the number of central high loft layers. For example, the absorbent core can comprise two high loft central layers as illustrated in FIG. 10 made of PET fibers and each having a thickness of ca. 0.50 mm, a basis weight of ca. 32 gsm and a density of ca. 0.065 g/cc.

The central layer 43 has a front edge 280, a back edge 282 and two longitudinally-extending side edges 284, 286. The front and back edges are typically shorter than the side edges. The front edge of the central layer corresponds to the edge intended to be placed towards the front edge of the absorbent article in which the core is or will be integrated. The superabsorbent material may be distributed in higher amount towards the front half of the central layer relative to the back half of the central layer. This is because there is typically more fluid discharged towards the front of the article in which a core will be incorporated. In addition to the profiled SAP distribution in the longitudinal direction (y), the SAP may be also be profiled in the transversal direction (x). Of course, the SAP may be also homogenously distributed in the transversal (x) and the longitudinal direction (y), which simplifies production: in that case any of the two shorter sides may be considered as the front edge and the opposite side will be the back edge. The absorbent cores may comprise one, two or more such high loft central layer. An absorbent core comprising two high loft central layers is discussed further below.

The central layer (or layers) serves as substrate for the SAP particles 60 which are blended between its fibers in at least one SAP containing zone 27. The central layer further comprises at least one longitudinally extending channel substantially free of SAP particles. This will be detailed further below. The SAP particles may be substantially uniformly blended across the thickness of the high loft nonwoven, but it is not excluded that the SAP particles may be more present on one side of the high loft nonwoven than the other, for example depending on the process of fabrication used.

Superabsorbent Material Particles

The central layer comprises a superabsorbent polymer (herein abbreviated as "SAP") in the form of particles 60 blended within the fibers of the high loft nonwoven layer. Any conventional SAP materials may be used. Typical SAP includes a variety of water-insoluble, but water-swellable polymers capable of absorbing large quantities of fluids. The term "superabsorbent polymer" refers herein to absorbent materials, which may be cross-linked polymeric materials, and that can absorb at least 10 times their weight of an aqueous 0.9% saline solution as measured using the Centrifuge Retention Capacity (CRC) test (EDANA method WSP 241.2-05E). The SAP may in particular have a CRC value of more than 10 g/g, or more than 20 g/g, or of from 20 g/g to 50 g/g, or from 25 g/g to 45 g/g.

The superabsorbent polymers are in particulate form so as to be flowable in the dry state and thus easily deposited on the substrate. Typical particulate absorbent polymer materials are made of poly(meth)acrylic acid polymers. However, it is not excluded that other polymer materials may also be used. The SAP particles may be relatively small (under 1 mm in their longest dimension) in their dry state and may be roughly circular in shape, but granules, fibers, flakes, spheres, powders, platelets and other shapes and forms are also known to persons skilled in the art. Typically, the SAP may be in the form of spherical-like particles.

As indicated previously, one advantage of the invention is that SAP particles having a relatively low permeability at equilibrium (UPM value) may be used. These particles are typically used in airfelt containing core because the cellulose fibers generally increase the permeability of the absorbent material. Airfelt free absorbent cores on the other hand typically require high permeability SAP to perform optimally. High permeability SAPs however are typically more costly than low permeability SAPs. The superabsorbent polymer particles used in the invention may thus have a UMP of below $30 \times 10^{-7}$ cm$^3 \cdot$s/g, in particular below $25 \times 10^{-7}$ cm$^3 \cdot$s/g, in particular below $20 \times 10^{-7}$ cm$^3 \cdot$s/g, in particular below $15 \times 10^{-7}$ cm$^3 \cdot$s/g, in particular from $1 \times 10^{-7}$ cm$^3 \cdot$s/g to $10 \times 10^{-7}$ cm$^3 \cdot$s/g as measured by the Urine Permeability Measurement Test indicated below in the "Test Procedure" section. The Urine Permeability Measurement Test has been originally disclosed in PCT application WO2012/174026A1.

Although it is not excluded that the absorbent core may comprise cellulose fibers, the absorbent core may in particular comprise no or only small amount of cellulose fibers, such as less than 20%, in particular less than 10%, 5% or even 0% of cellulose fibers by weight of the absorbent core. The absorbent material may thus consist or consist essentially of SAP. For the purpose of determining the amount of cellulose fibers in the absorbent core, any paper or tissue paper layer serving as top layer, bottom layer or wrapping layer are disregarded.

Channel

The central layer 43 comprises at least one (in particular one, two or more) longitudinally-extending zones 26 substantially free of SAP particles 60. These zones are considered, as seen as in FIGS. 1 and 6, from above in the plane formed by the transversal and longitudinal directions. These one or more zones substantially free of SAP particles are referred to herein as "channels". For convenience, the plural form will be used even if there is only one of these zones. The rest of the central layer outside the channels 26 defines at least one zone 27 having superabsorbent polymer particles 60.

By "substantially free of SAP", it is meant that the basis weight of the SAP material in each of these zones is at least less than 25%, in particular less than 20%, in particular less than 10%, of the average basis weight of the SAP in the central layer as a whole. The channels may in particular be zones of the central layer where there are no SAP particles. In this regard, minimal amount such as involuntary contaminations with SAP particles that may occur during the making process are not considered as absorbent material.

The channels extend longitudinally in the central layer. By "longitudinally extending", it is meant that the channels extend more in the longitudinal direction (y) than in the transversal direction (x). The channels may for example have a length (projected on an axis parallel to the longitudinal direction) which is at least 5%, in particular from 10% to 70%, or from 15% to 60% of the length of the central layer. The channels 26 may be oriented parallel to the longitudinal direction, as shown in FIG. 1. However it is not excluded that the channels may be curved, in particular concave towards the longitudinal axis—as in inverted brackets:) (as indirectly shown on FIG. 9—or straight and tilted at an angle relative to the longitudinal direction. The channels may be advantageously spaced away from the longitudinally extending side edges 284, 286 of the central layer. In this way, the SAP particles along the longitudinal side edges provide a barrier for the fluid in the channels before it reaches the side edges of the central layer. The channels 26 may be for example spaced at a distance of at least 5 mm from the side edges of the central layer. The central layer may comprise at least two channels placed symmetrically on each side of the longitudinal centerline, as illustrated by the channels 26 in FIG. 1 and FIG. 6. There may be of course only one channel, or alternatively more than two channels, for example three channels, or two pairs of channels, present. Advantageously the channels are symmetrically disposed relative to the longitudinal axis of the core.

The channels may extend along the whole length of the central layer 43, thus extending from the front edge 280 of the central layer to the opposed back edge 282. This is illustrated in FIG. 1 for example. On the other hand, it is also considered that the channels may also be spaced away (for example at least by 5 mm) from the front edge and/or back edge of the central layer. This is illustrated in FIG. 6, and in this configuration the channels are entirely surrounded by the SAP particles present in the rest of the central layer. This provides an additional leakage barrier at the front and back edges of the central layer. The channels extending up to the front and back edges of the central layer may be on the other hand easier to make. Channels extending to the side edges of the core 284 and 286 (not represented) may on the other hand be beneficial for example to provide better comfort between the legs of the wearer of the absorbent article.

Bottom Layer and Top Layer

The central layer is sandwiched between a top layer 41 and a bottom layer 42. The top layer is on the side of the core intended to be placed closest to the wearer-facing side of the absorbent article. The top layer is thus liquid-permeable, so that a fluid can easily reach the central layer through the top layer during use. The bottom layer is positioned on the other side of the central layer. It may be liquid-permeable or liquid impermeable. The top layer and the bottom layer provide a cover on both sides of the central layer for preventing the SAP particles from falling out of the high loft during the core and article making process as well as during use of the absorbent article.

The top and bottom layers may be made of a relatively thin and cheap material, as are commonly used for the production of conventional cores. The top and bottom layers may be for example a tissue paper (airfelt or wetlaid) having a basis weight ranging for example from 5 to 100 gsm, in particular 10 to 40 gsm. The top and bottom layers may also be formed from a low basis weight nonwoven web having a basis weight of between 5 gsm and 30 gsm, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 20 gsm. Such materials are for example disclosed in U.S. Pat. No. 7,744,576, US 2011/0268932 A1, US 2011/0319848 A1 and US 2011/0250413 A1. Nonwovens materials are typically inherently hydrophobic, and the top layer may thus be treated to render it hydrophilic, for example by treating it with a surfactant or other methods as is known in the art. The top layer and the bottom layer may be made of the same or different material, optionally with the top layer or bottom layer treated differently to render to the top layer more hydrophilic than the bottom layer.

Figure 3:
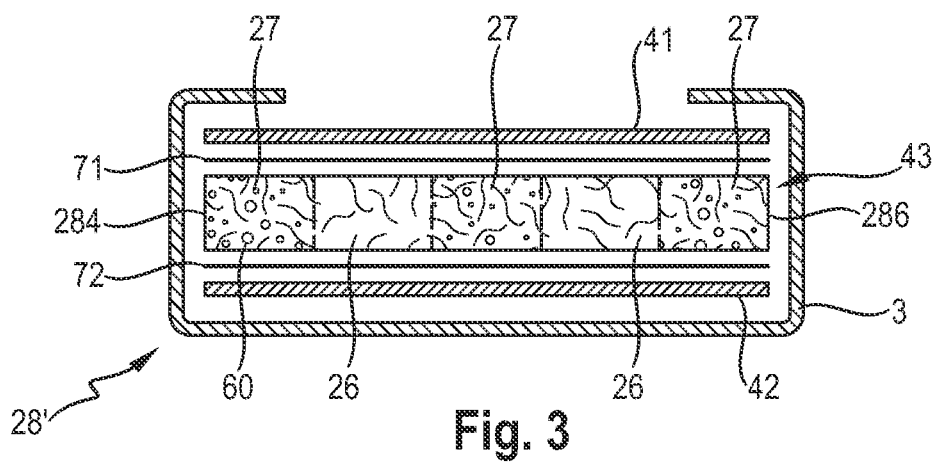
FIG. 3 shows a cross-sectional view of the absorbent core of FIG. 1 with a wrapping layer.

In addition to the top layer and the bottom layer, the absorbent core can further comprise a wrapping layer 3 forming a C-wrap around the longitudinally extending side edges 284, 286 of the core, as shown in FIG. 3. By "C-wrap", it is meant that the layer covers at least the top side or bottom side of the core, extends along its side edges to form flaps that are then folded and attached, typically by gluing, over the opposite side of the core. The wrapping layer 3 may thus have a cross-section similar to the letter C (when rotated 90°). A C-wrap construction may further help containing the SAP particles during the making or wearing of the absorbent article. The wrapping layer may for example be made of a low basis weight nonwoven layer, for example having a basis weight of from 5 to 40 gsm, in particular from 8 to 25 gsm, in particular a SMS nonwoven, but other materials are of course possible. The wrapping layer 3 has been represented in FIG. 3 as extending from the bottom side of the core and having flaps folded over the top side of the core. The inverted configuration is also possible, with the C-wrapped layer 3 extending from the top side and with the flaps folded over the bottom side. The folded flaps may end and be attached in the vicinity of the longitudinally extending side edges of the core or may be longer than represented to that they overlap and attached to another. It is also considered that a C-wrap construction may be formed by one of the top layer or bottom layer extending transversally along the longitudinally extending side edges of the core and forming flaps as described for the wrapping layer 3. The presence of a wrapping layer is optional.

The top layer 41 and/or the bottom layer 42 may be attached to the central layer 43. A layer of glue 71 may be for example applied between the top layer and the central layer 43. Any type of conventional glue and glue application method may be used. Typically a hot melt glue may be uniformly sprayed on the substantially the whole of the surface of the layers before putting the two layers in close contact so that they become attached. The glue may also be applied by a contact method to one of the layers, in this case in particular the top or bottom layer, typically by slot-coating a series of parallel thin lines of glue in the machine direction (y direction). A layer of glue 72 may also be similarly applied between the bottom layer 42 and the central layer 43.

The top layer and/or the bottom layer may also be specifically and additionally attached to the central layer in the channel zones 26, for example to maintain the channels relatively free of AGM during manufacturing and use of the absorbent article. Such an attachment in the zones of the channels can be achieved via any known attachment means such as gluing, pressure bonding, ultrasonic bonding, heat bonding or combination thereof. This further attachment may compress or crimp of the central layer in the channels, thus providing three dimensional channels already before the core has accepted fluid, which may for example serve as folding guides for the core.

Process

Figure 4:
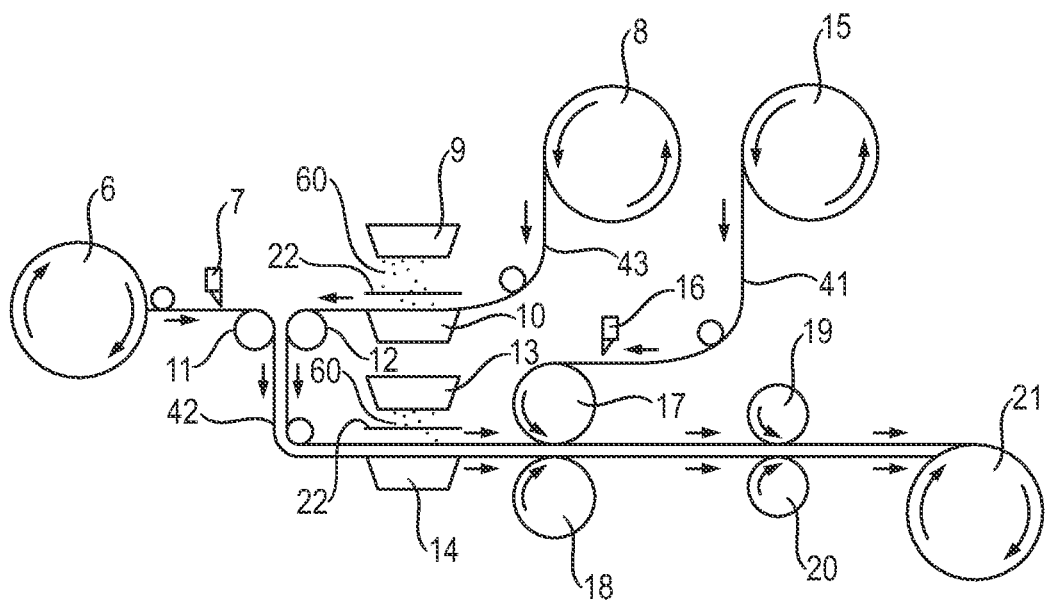
FIG. 4 shows a schematic view of the process for making the absorbent core of FIG. 1.

A continuous process for making the absorbent cores as illustrated in FIG. 1 will now be described with reference to FIG. 4. The various arrows in FIG. 4 represent the rotational directions of the various roll-releasing cylinders and roll-winding cylinders and the running directions of the manufacturing materials during the production flow process. Other processes and modifications are possible and will further be discussed below.

Figure 5:
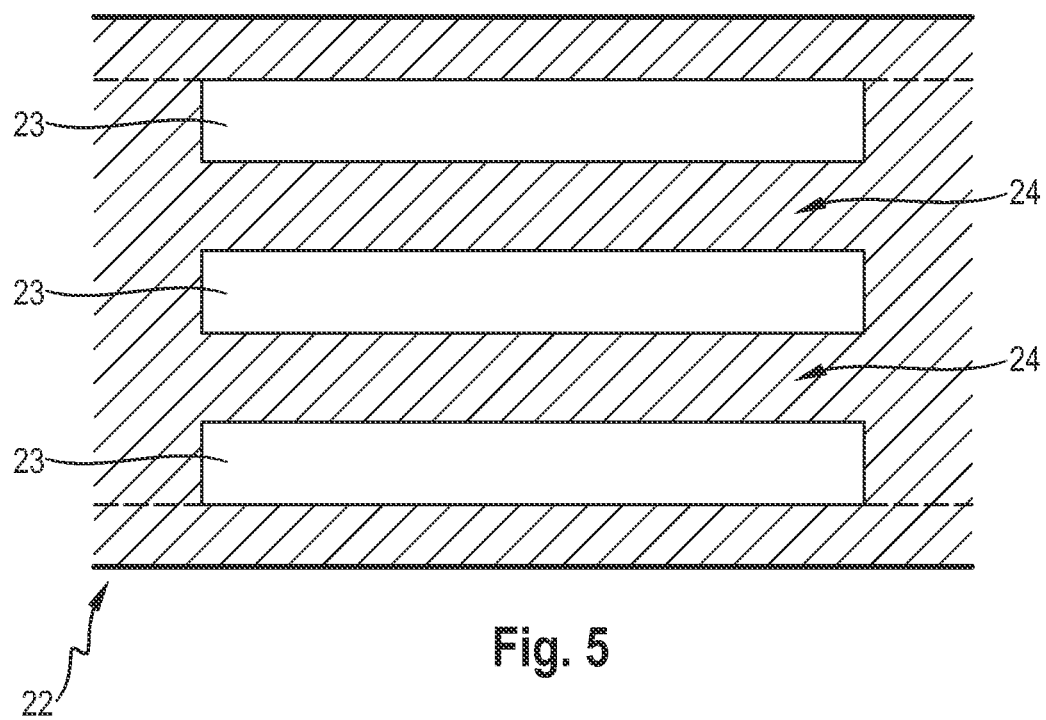
FIG. 5 shows an exemplary shielding plate for use in the process of FIG. 4.

As illustrated in FIG. 4, the apparatus for making the absorbent cores includes a bottom layer web unwinder 6, a bottom layer glue spraying head 7, a high loft central layer web unwinder 8, a first SAP particles sieve plate 9 and vacuum suction box 10, a first pair of hot press rollers 11 and 12, a second SAP particles sieve plate 13 and vacuum suction box 14, a top layer web unwinder 15, a top layer spraying head 16, second pair of hot press rollers 17 and 18, trimming off knives 19, 20, and a product roll winding roller 21. As will be discussed further, a shielding plate 22, illustrated in FIG. 5 is placed between each sieve plates 9, 13 and the central layer 43 to provide that the desired channels zones of the central layer remain substantially free of SAP particles. The vacuum suction box 10 and 14 may also comprise a blind area (area without vacuum) to reduce SAP deposition in the channels zones.

The first SAP particles sieve plate 9 and the second SAP particles sieve plate 13 may be both provided with a frequency changing and speed adjusting device (not drawn in FIG. 4). The frequency changing and speed adjusting devices of the first and second SAP sieve plates 9, 13 are adjusted to maintain a vibration frequency that matches the product roll winding roller 21 linear velocity and to ascertain that the sprayed polymer water absorbing resin (SAP) is mostly uniformly distributed on the bulky nonwoven fabric 43.

During production, a roll of bottom layer material, for example a paper or nonwoven roll, is installed on the bottom layer web unwinder 6. A high loft nonwoven fabric roll is installed on the central layer web unwinder 8. The SAP particles are charged in the first and second SAP particles sieve plates 9 and 13. A roll of top layer material, which can be a paper or nonwoven roll, is installed on the top layer web unwinder 15. During the continuous process of making the absorbent cores, the bottom layer 42 passes through the spraying head 7 and is applied on one side with a glue 72, before being attached to the central layer 43 between the first press rollers 11 and 12. The high loft nonwoven central layer 43 passes through the first SAP particles sieve plate 9 and vacuum suction box 10, wherein the SAP particles are deposited into the central layer and blended into the fibers the central layer from a first side. The shielding plate 22 and blinded areas, if present, on the suction box 10 provide that no or a limited amount of SAP is deposited into the channels zones of the central layer that are intended to remain substantially free of SAP particles. It is also possible that the bottom layer material 6 is first attached to on a first side of the central layer 43 before the SAP particles 60 are deposited onto and blended between the fibers of the central layer.

After the bottom layer 42 and the central layer 43 have been attached between the rollers 11 and 12, these combined layers may optionally pass between a second SAP particles sieve plate 13 and vacuum suction box 14 that cooperate to deposit SAP particles onto the second surface of the central layer and blend the SAP particles in the fibers of the central layer from this second surface. Again, a second shielding plate 22 which can be similar to the first shielding plate can be used to provide that the desired channels zones 26 of the central layer remain substantially free of SAP particles. The top layer 41 which has been applied with an adhesive 72 by a glue spraying head 16 is then joined to the central layer to cover the second surface of the central layer between two press rollers 17 and 18. Of course in the preceding the top layer and bottom layer may be used interchangeably.

The press rollers 17 and 18 may have a substantially flat surface, or they may have elevated areas where extra pressure and heat should be applied onto the core. These elevated areas may coincide with the channel areas, and thus provide a mechanical bonding, ultrasonic bonding and/or heat bonding within the channel zones 26. The press rollers 11-12, 17-18 may be heated. It is also possible that the rollers have elevated areas along the longitudinal side edges and/or the back and front edges (360° perimeter) the core. A better bonding can be achieved in these zones when they are free of SAP as in the channel zones 26. Trimming knives 19 and 20 can be provided to trim the longitudinal side edges of the continuous band of absorbent core before the stream of the absorbent core material is finally rolled into a roll of absorbent core material by the product roll winding roller 21.

The roll of absorbent core material thus formed may be stored or transported to an article production site where it is further converted into an absorbent product. It is also possible that instead of forming a roll, the stream of absorbent core material may be directly fed into a converting line, in which case the absorbent cores will be individualized by cutting along their front and back edges.

A wrapping layer 3 (not represented in FIG. 4) may also be fed before the core material is rolled to wrap the top, central and bottom layer as shown discussed in relation to FIG. 3 to prevent losses of SAP though the side edges of the absorbent core. Alternative such wrapping layer may also be attached to the core when further converting the core material web.

The process and apparatus discussed above is generally similar to the one disclosed in CN101797201, except for the presence of a static shielding plate 22 between the sieving plate 9 (respectively 13) on one side, and the central layer 43 placed on the vacuum suction box 10 (respectively 14) on the other side. The shielding plate may be a piece of metal comprising elongated cut-out zones 23 through which the SAP particles can flow and with full zones 24 between the cut-out zones 23, as illustrated in FIG. 5. As the central layer (represented by the dashed lines) passes underneath the shielding plate, the SAP particles are deposited through the cut-out zones 23 and leave the zones of the central layer directly situated under the shielding plate substantially free of absorbent material. Also not disclosed in CN101797201 is the optional usage of patterned pressure rolls 17 and 18 that can provide mechanical bonding, ultrasonic bonding and/or heat bonding of the core layers in the channels.

Instead of a sieving plate/shielding plate system as disclosed in FIG. 4, it is also possible to deposit the SAP in the desired areas 27 by using a plurality of SAP applicators or SAP chutes offset in cross-machine direction and working in parallel. The applicators or chutes have a gap between them so that the channel zones between them are not deposited with SAP particles. For example three applicators or chutes having two gaps between them would provide a deposition pattern as for the core of FIG. 1. It is also possible to use a SAP printing system to apply the SAP on both or one sides of the central layer, such a SAP printing system is discussed in the next section with reference of FIG. 8.

Channel Surrounded by a SAP Containing Zone

FIG. 6 illustrates an absorbent core 28a according to the invention having channels 26 not extending to the front edge 280 and back edge 284 of the central high loft layer 43. The channels 26 are therefore fully surrounded by a zone 27 of the central layer comprising SAP particles. The rest of the absorbent core construction can be the same as previously disclosed in relation with FIG. 1, for example there may be a glue layer 71 between the top layer and the central layer, and another glue layer 72 between the central layer and the bottom layer. The channels are shown straight and parallel to the longitudinal axis, but curved channels may be provided instead, in particular the channels may comprise at least one pair of channels on each side of the longitudinal axis and having a curvature which is concave towards the longitudinal axis. i.e. like inverted brackets:) (.Having such curved channels may provide for better comfort when after the core has been loaded with a fluid as the channels will generally follow the contour of the legs of the wearer.

Such absorbent cores may be produced as previously described in relation to FIG. 4, with the difference that the shielding plates are mobile to follow the web of central layer passing beneath it. The SAP particles exiting the sieving plate may pass through a shielding plate which is mounted on a rotating drum or a rotating belt. The rotating plate comprise a cut-out section through which the SAP particles can pass and deposit onto the central layer, and full zones which prevent the SAP particles from depositing onto the zones of the central layer immediately beneath the full zones. Several shielding plates are mounted on each moving rotating drum or belt and the shield plates move at the same speed as the web of high loft material underneath it so that the pattern of SAP distribution on the central layer generally corresponds to the pattern formed by the cut-out and full zones of the plates. However this technique may be difficult put in place to obtain precise deposition at high speed.

Figure 8:
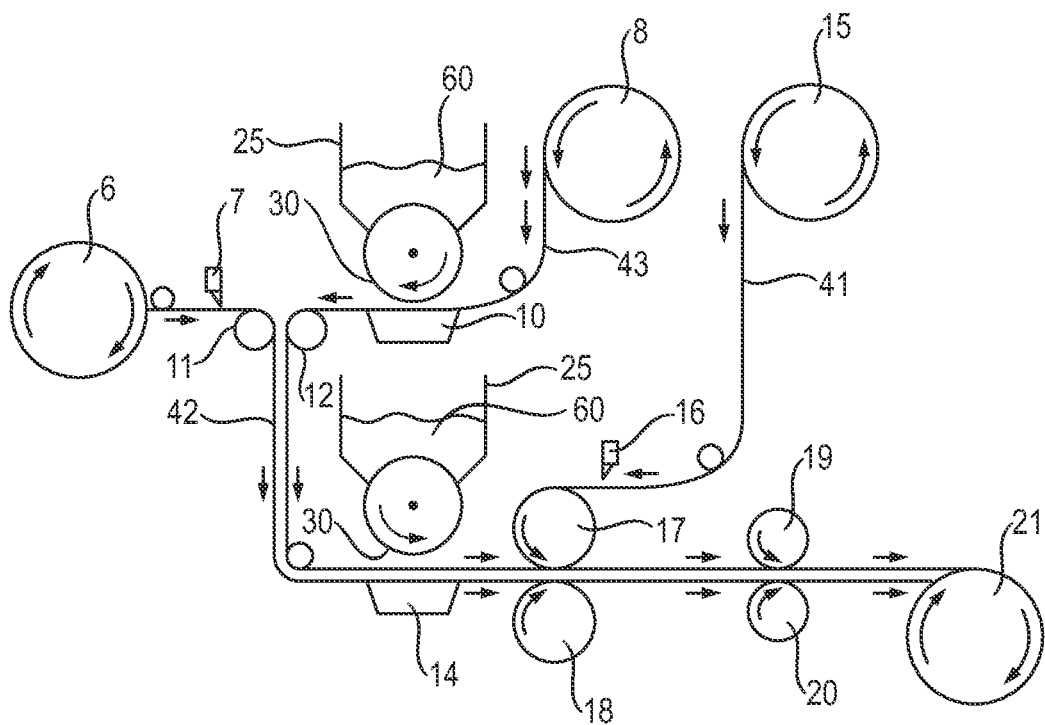
FIG. 8 shows a schematic view of the process for making the absorbent core of FIG. 6, using SAP printing rolls.

The SAP particles may be instead deposited a SAP printing technology, which allows relatively precise deposition of SAP particles in desired areas at relatively high speed. In particular the SAP printing technology as disclosed for example in US2006/24433 (Blessing), US2008/0312617 and US2010/0051166A1 (both to Hundorf et al.), and in particular WO2012170798A1 (Jackels) may be used. As illustrated in FIG. 8, this technique uses a printing roll 30 to deposit the SAP particles onto a substrate (in this case the high loft central layer 43) disposed on a grid of a support (represented as vacuum box 10 but it may also be a circular rotating lay-on drum roll as taught in the references above). A feeder 25 feeds the SAP particles to the external surface of the printing roll comprising at least one reservoir 32 and typically a plurality of reservoirs disposed on the circumference of the printing rolls. Each reservoir 32 comprises at least one raised strip 31, which may have a corresponding mating strip on the lay-on drum roll, and a plurality of grooves and/or cavities (not represented) between the raised strips having a void volume, for receiving the absorbent material.

The SAP particles are fed from the feeder into the grooves or cavities of the reservoir except in the area of the raised strips. The particles are then transferred onto the high loft nonwoven layer, for example by a combination of vacuum on the deposition side and overpressure on the printing roll side at the meeting point. The absorbent material may also be deposited at different basis weight in selected areas by varying the volumes or numbers of the grooves or cavities, so that, for example there is higher amount of absorbent material towards the front edge of the core than towards the back edge. This is disclosed in details in the references indicated above. The advantages of the SAP printing system is that the channels may be clearly defined by the raised surfaces on the printing roll, and may provide channels having a shape that is not straight, for example curved as illustrated by the curved raised strips 31 on FIG. 9.

The processes disclosed herein show the SAP particles deposited in two steps, one step for each side of the central layer. However it is also possible that the SAP particles are only deposited once, on a single side of the central layer, by removing one of the deposition devices. While in this case the SAP distribution may be less homogeneous in the thickness dimension of the central layer, this has the advantage of simplifying the making process of the core. It is also possible to first attach the central layer 43 to the top (or bottom) layer 42 before depositing the first SAP particles.

Another process (not represented) for making a core of the invention is to punch or otherwise cut at least one piece of material in the central layer corresponding to the channels 26 before attaching it to the bottom and top layers. The SAP can then be homogenously deposited by any methods on the punched or cut-off high loft central layer. The SAP particles falling through the holes can then for example be recycled to the feeder. The other processes described have however the advantages that the high loft material is present in the channels and thus provide stability in the channel regions of the core.

Absorbent Core

The absorbent cores discussed previously comprise a single high loft nonwoven layer, however it is also possible that the absorbent cores comprise two (or more) high loft nonwoven layers between the top and bottom layers. The absorbent core thus may comprise a first central layer and a second central layer, each of which being a high loft fibrous nonwoven layer comprising superabsorbent polymer particles blended between their fibers.

This is illustrated for example in FIG. 10 wherein the first central layer 431 and the second central layer 432 are shown sandwiched between the top layer 41 and the bottom layer 42. Each and in particular both of the first and the second central layers may comprise one, two or more longitudinally-extending channels 26, the channels being as indicated before. In particular the channels may extend to the front and back edges of their central layer, or may be surrounded by a zone comprising SAP. The channels in one central layer may generally correspond to the channel in the other central layer. This is for example represented in FIG. 10. In the plan of the core (not shown), these channels in each central layer may have the same configuration as those discussed in FIG. 1 and FIG. 6 for example. The general indications made generally in the previous sections also apply to an absorbent core having a dual central layer. Such absorbent cores may also comprise a wrapping layer as previously discussed.

As illustrated in FIG. 10 the channels in each central layer may be registered and thus match each other but it is not excluded that the channels of one layer may be completely or partially shifted transversally relative to the channels of the other layer. It is also considered than only one of the central layer may have channels according to the invention. For example, only the first central layer 431 closest to the top layer of the core may comprise the channels, and the second central layer 432 may be absent of channels, in other words may comprise SAP over its entire area. This may provide for a quicker absorption of the fluid into the core. It is also possible that the high loft central layers have different basis weight, density and/or amount of AGM deposited. For example the permeability in the upper central layer may be enhanced by using a low basis weight high loft and softness may be enhanced in the bottom layer with a denser high loft material. Of course other configurations are also possible. The two or more two central layers can be of equal dimensions in the plane of the core, but they may also have different length and/or width. Two central layers of unequal length could be beneficial to provide different amount of SAP along the absorbent core, and made for example by adding a cut and slit unit on the second layer patch, and before combining it with the first layer.

It is also considered that the two high loft central layers may comprise different sort of SAP, for example faster absorbing SAP (higher UPM value) in the first central layer 431 closer to the top layer and/or a more absorbing SAP (higher CRC) in the second central layer 432. The channels may have different shapes in each high loft central layers. For these reasons, an intermediate nonwoven or paper layer (not represented) can be placed between the two central layers to avoid that the SAP particles deposited on the one central layer fall into the other central layer. Such intermediate layers may be attached to one or both of the central layers by any know means, for example by gluing.

Figure 9:
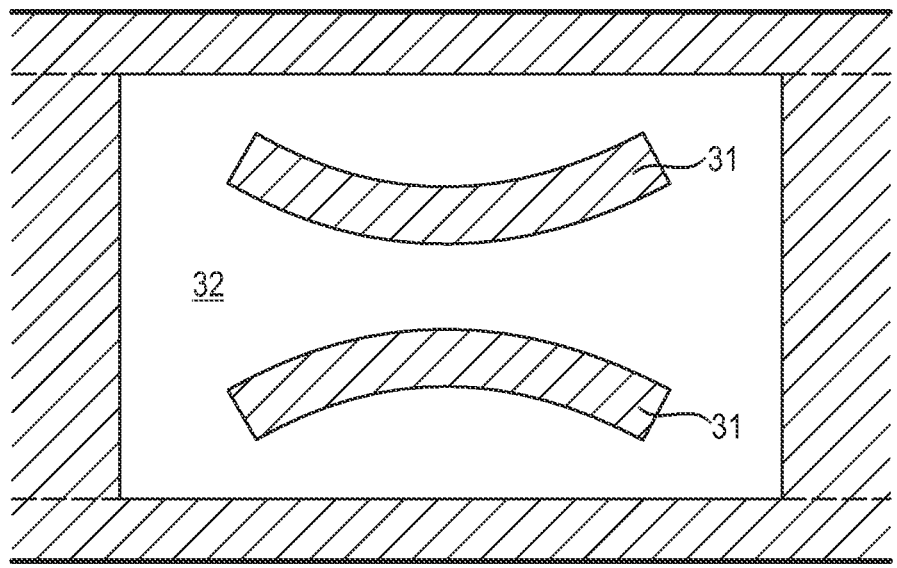
FIG. 9 illustrates the surface of a SAP reservoir of a printing roll comprising two curved raised strips.
Figure 11:
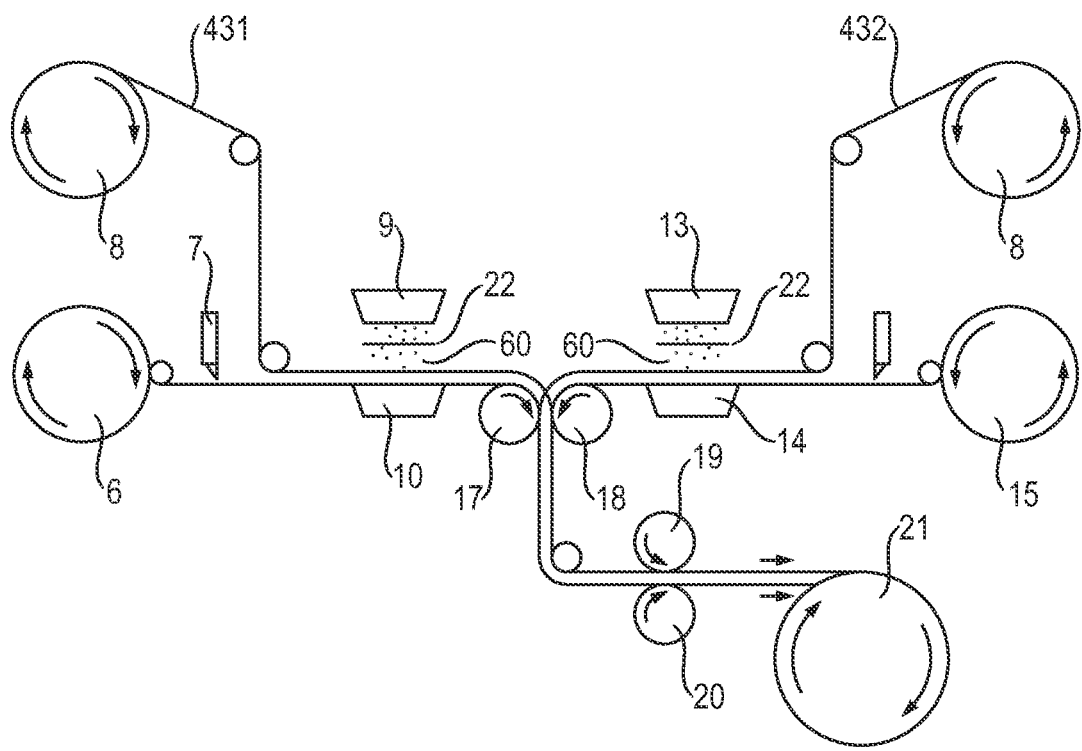
FIG. 11 shows a schematic view of the process for making the absorbent core of FIG. 10.

Absorbent cores comprising a dual high loft nonwoven layers may be made by a method adapted from one of the methods disclosed with reference to FIG. 4 and FIG. 8. Two separate high loft layer releasing cylinder 8 may be provided to provide for the first and second high loft central layers 431, 432, as shown in FIG. 11. As an alternative, a high loft web having a double width may be used: such a large width roll can be cut after release in machine direction in two halves providing for two streams of high loft nonwoven material that are then separately deposited with SAP particles. The two stream of high loft material 431, 432 may be then combined separately with the top layer and bottom layer respectively, each having then SAP particles 60 deposited onto them through a suitable SAP deposition device. As discussed previously, each SAP deposition device may for example comprise a static or mobile shielding frame 22 (as represented in FIG. 11) or a printing roll system as illustrated in FIGS. 8-9. It is also possible to deposit and blend the SAP into the fibers of only one of the first and second the central layer.

Absorbent Article

Figure 12:
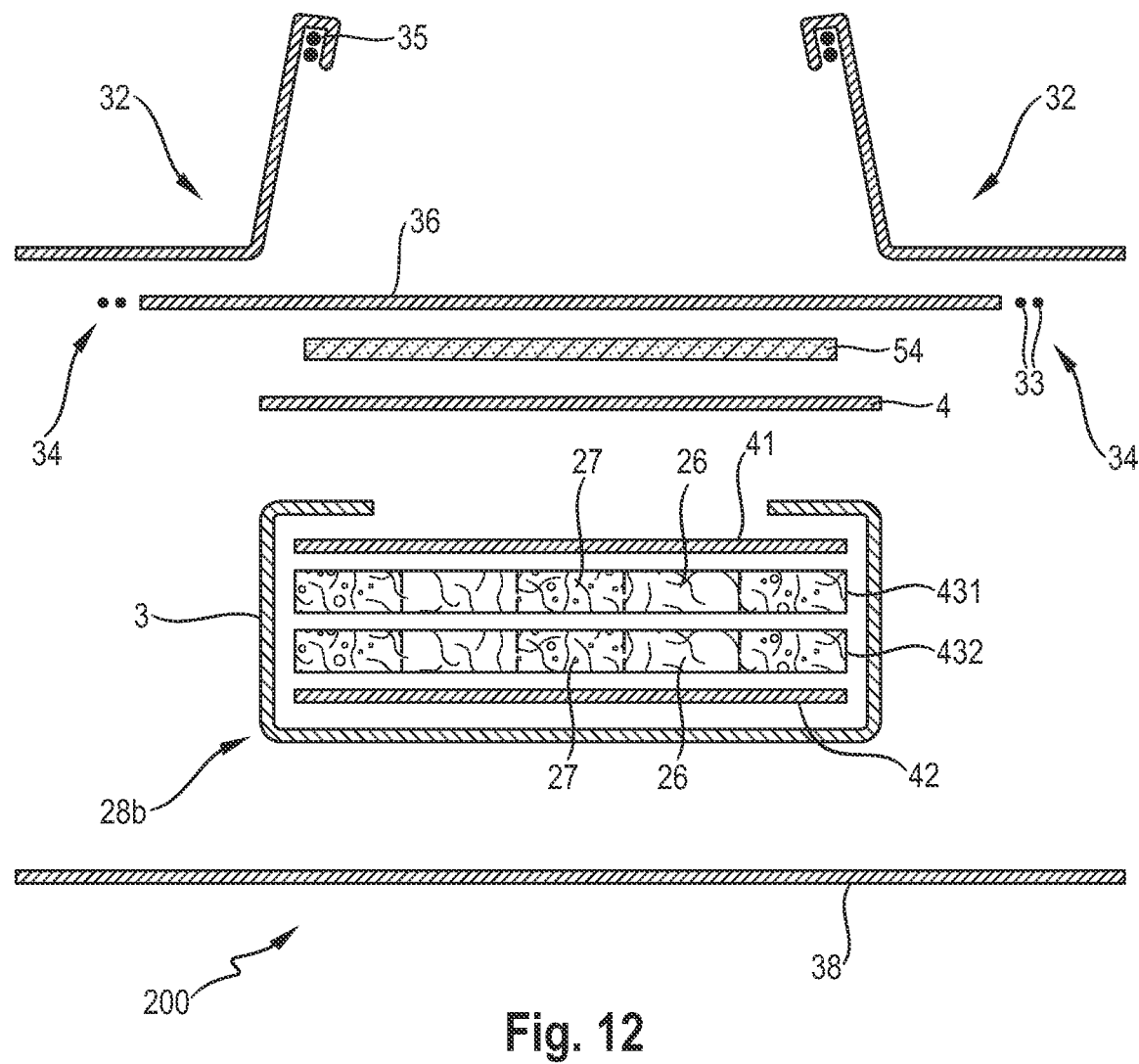
FIG. 12 is a schematic cross-sectional side view of an absorbent article comprising the absorbent core of FIG. 10 with a wrapping layer.

The absorbent cores may be incorporated into any kind of personal hygiene articles, which may be for example a baby diaper or a training pant. A schematic cross-sectional view showing some of the main components of a taped diaper absorbent article 200 is illustrated in FIG. 12. In this Figure, the absorbent core of FIG. 10 (with a wrapping layer 3) is shown, but this is of course not limiting and for illustration only. Absorbent articles typically comprise a wearer-facing fluid permeable topsheet 36 and a garment-facing liquid impermeable backsheet 38 attached to each other along their perimeter. The absorbent core is placed between these layers and may be attached directly and indirectly to these layers, typically by gluing or heat/pressure bonding.

The topsheet 36 is preferably compliant, soft-feeling, and non-irritating to the wearer's skin. Further, at least a portion of the topsheet is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet includes fibers, the fibers may be spunbond, carded, wet-laid, meltblown, hydroentangled, or otherwise processed as is known in the art, in particular spunbond PP nonwoven. Typical diaper topsheets have a basis weight of from about 10 gsm to about 28 gsm, in particular between from about 12 gsm to about 18 gsm but other basis weights are possible.

The backsheet 38 is typically impermeable to liquids (e.g. urine). The backsheet may for example be or comprise a thin plastic film such as a thermoplastic film having a thickness of less than about 0.10 mm. Exemplary backsheet films include those manufactured by Tredegar Corporation, based in Richmond, VA, and sold under the trade name CPC2 film. Other suitable backsheet materials may include breathable materials which permit vapors to escape from the article while still preventing exudates from passing through the backsheet. A covering low basis weight nonwoven may be attached to the external surface of the film to provide for a softer touch.

The absorbent articles may also comprise a liquid management layer 54 (also called fluid acquisition or fluid distribution layer) directly under the topsheet 36. The function of such a layer is to rapidly acquire the fluid from the topsheet away from the wearer-facing side and/or to distribute over a larger area so it is more efficiently absorbed by the absorbent core. It is also possible that such a liquid management layer may be placed between the backsheet and the absorbent core. A further layer 4 may be present between the liquid management 54 and the absorbent core 28. The further layer 4 may be another such acquisition or distribution layer, or may be a tissue paper or low basis weight NW layer that provides an additional wrapping of the absorbent core 28 to avoid SAP particles from escaping outside the core.

Absorbent articles such as diapers or training pants may typically further comprise components that improve the fit of the article around the legs of the wearer, in particular barrier leg cuffs 32 and gasketing cuffs 34. The barrier leg cuffs may be formed by a piece of material, typically a nonwoven, which is partially bonded to the rest of the article and can be partially raised away and thus stand up from the plane defined by the topsheet. The barrier leg cuffs are typically delimited by a proximal edge joined to the rest of the article, typically the topsheet and/or the backsheet, and a free terminal edge intended to contact and form a seal with the wearer's skin. The standing up portion of the cuffs typically comprise an elastic element, for example one or a plurality of elastic strands 35. The barrier leg cuffs provide improved containment of liquids and other body exudates approximately at the junction of the torso and legs of the wearer.

In addition to the barrier leg cuffs, the article may comprise gasketing cuffs 34, which are formed in the same plane as the chassis of the absorbent article, in particular which may be at least partially enclosed between the topsheet or the barrier leg cuffs and the backsheet, and may be placed laterally outwardly relative to the upstanding barrier leg cuffs. The gasketing cuffs can provide a better seal around the thighs of the wearer. Usually each gasketing leg cuff will comprise one or more elastic string or elastic element 33 comprised in the chassis of the diaper for example between the topsheet and backsheet in the area of the leg openings.

The absorbent articles may also include other typical components found in diapers, training pants or adult incontinence products (and not further represented). A releasable fastening system for taped diapers may be provided to provide lateral tensions about the circumference of the absorbent article to hold the absorbent article on the wearer. This fastening system is not necessary for training pants since the waist region of these articles is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region of the article for the fastener to be releasably attached.

The absorbent article may comprise front ears and back ears as is known in the art. The ears can be integral part of the chassis, for example formed from the topsheet and/or backsheet as side panel. Alternatively, they may be separate elements attached by gluing and/or heat embossing. The back ears are advantageously stretchable to facilitate the attachment of the tabs on the landing zone and maintain the taped diapers in place around the wearer's waist. The front ears may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. The bonding between components is for clarity and readability not represented in the majority of Figures, in particular FIG. 12. Adjacent layers of the article should be considered to be attached to another unless specifically mentioned otherwise. For example the backsheet and the bottom layer of the absorbent core may be typically glued together. The adhesives used may be any standard hotmelt glue as known in the art.

Packaging

The absorbent articles may be packaged in any type of conventional packaging. The absorbent articles may be in particular compressed when packaged to save space. In particular the package may comprise a plurality of the absorbent articles, wherein the package has an in-bag stack height of less than about 80 mm, according to the In-Bag Stack Height Test as described in U.S. Pat. No. 8,585,666 B2 (Weismann), incorporated herein by reference. Alternatively, packages of the absorbent articles of the present disclosure may have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test.

Test Procedures

The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2-05.

Urine Permeability Measurement (UPM) Test Method

This method determines the permeability of a swollen hydrogel layer 1318.

Figure 13:
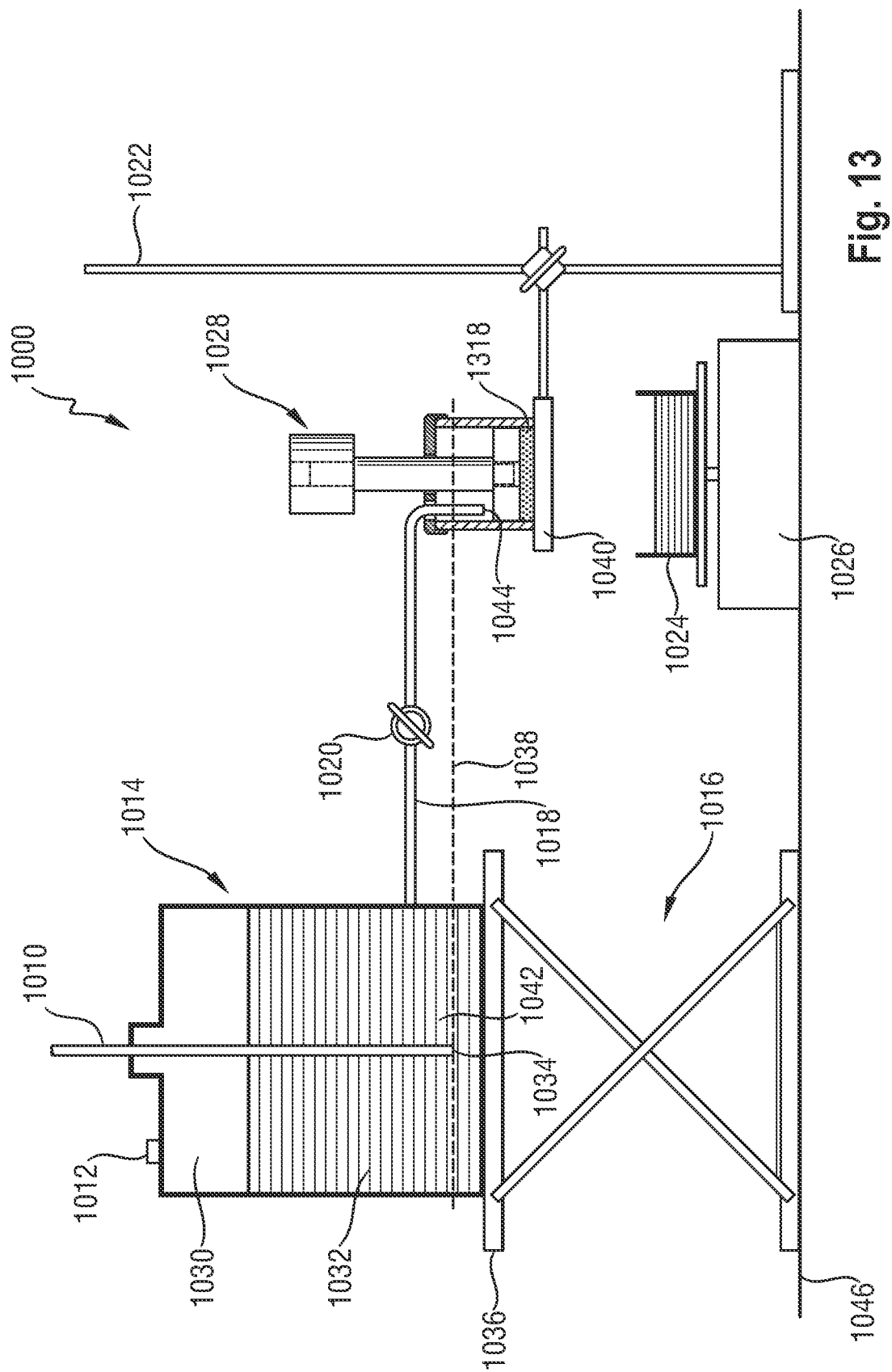
FIG. 13 is a partial cross-sectional side view of a suitable permeability measurement system for conducting the Urine Permeability Measurement Test.

FIG. 13 shows a permeability measurement system 1000 set-up with the constant hydrostatic head reservoir 1014, open-ended tube for air admittance 1010, stoppered vent for refilling 1012, laboratory jack 1016, delivery tube 1018, stopcock 1020, ring stand support 1022, receiving vessel 1024, balance 1026 and piston/cylinder assembly 1028.

Figure 14:
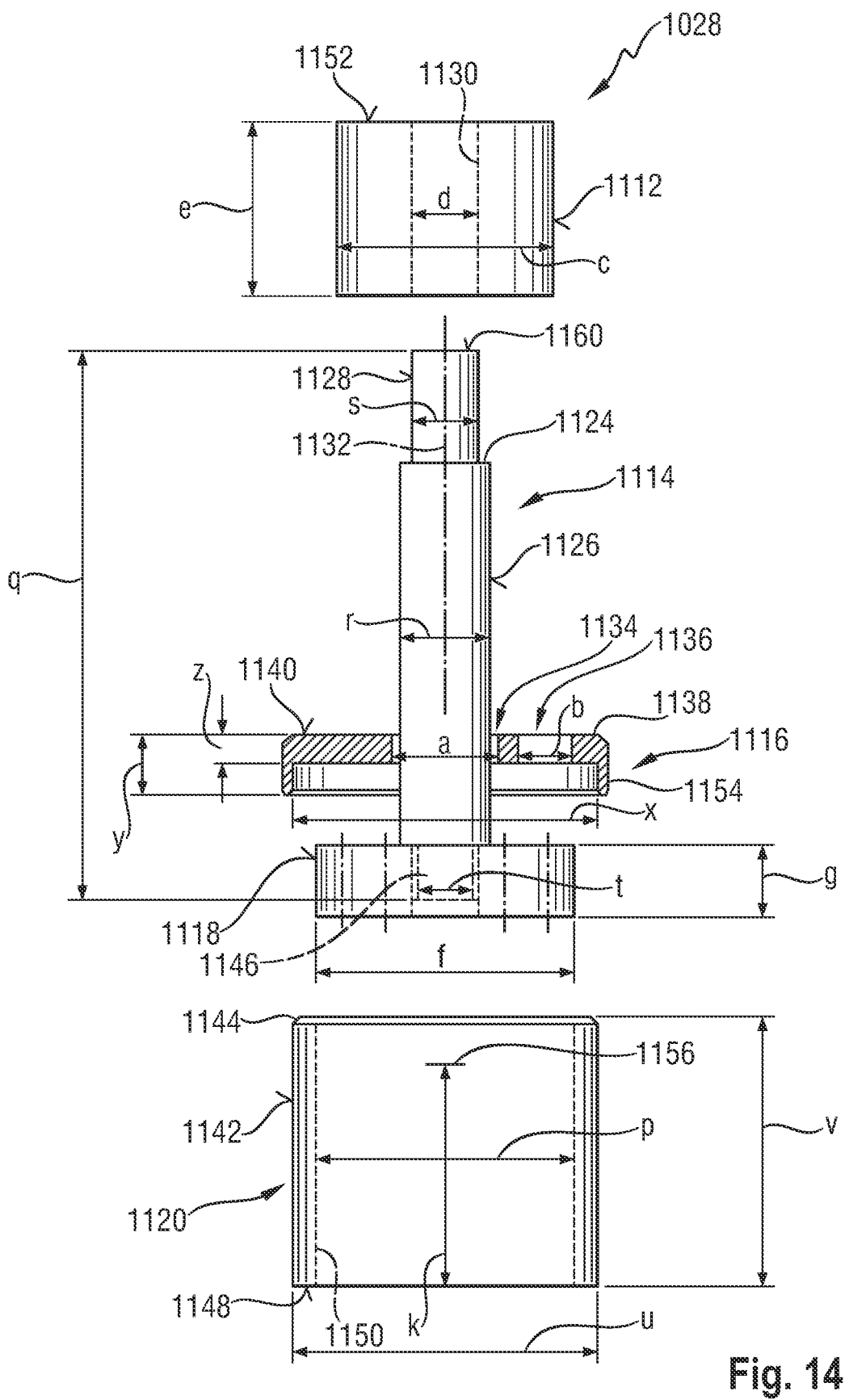
FIG. 14 is a cross-sectional side view of a piston/cylinder assembly for use in conducting the Urine Permeability Measurement Test.
Figure 15:
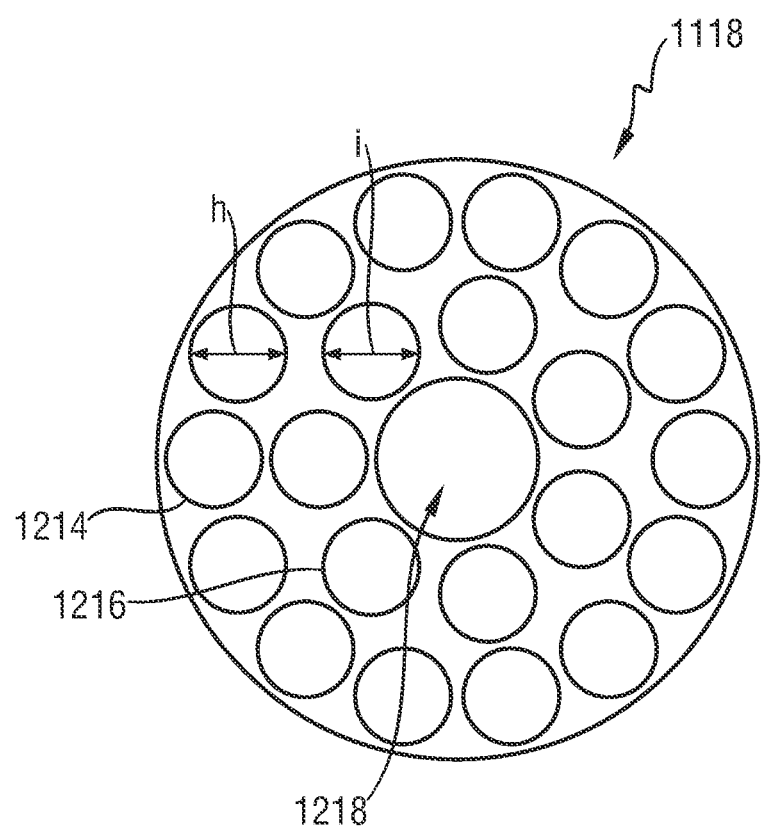
FIG. 15 is a top view of a piston head suitable for use in the piston/cylinder assembly shown in FIG. 14.

FIG. 14 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm2) with inner cylinder walls 1150 which are smooth. The bottom 1148 of the cylinder 1120 is faced with a US. Standard 400 mesh stainless-steel screen cloth (not shown) that is bi-axially stretched to tautness prior to attachment to the bottom 1148 of the cylinder 1120. The piston shaft 1114 is made of transparent polycarbonate (e.g., LEXAN®) and has an overall length q of approximately 127 mm. A middle portion 1126 of the piston shaft 1114 has a diameter r of 21.15 mm. An upper portion 1128 of the piston shaft 1114 has a diameter s of 15.8 mm, forming a shoulder 1124. A lower portion 1146 of the piston shaft 1114 has a diameter t of approximately 5/8 inch and is threaded to screw firmly into the center hole 1218 (see FIG. 15) of the piston head 1118. The piston head 1118 is perforated, made of transparent polycarbonate (e.g., LEXAN®), and is also screened with a stretched US. Standard 400 mesh stainless-steel screen cloth (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi (2.07 kPa) over the area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be re-positioned with the same orientation relative to one another for each measurement.

The cylinder 1120 specification details are:
Outer diameter u of the Cylinder 1120: 70.35 mm
Inner diameter p of the Cylinder 1120: 60.0 mm
Height v of the Cylinder 1120: 60.5 mm
The cylinder lid 1116 specification details are:
Outer diameter w of cylinder lid 1116: 76.05 mm
Inner diameter x of cylinder lid 1116: 70.5 mm
Thickness y of cylinder lid 1116 including lip 1154: 12.7 mm
Thickness z of cylinder lid 1116 without lip 1154: 6.35 mm
Diameter a of first lid opening 1134: 22.25 mm
Diameter b of second lid opening 1136: 12.7 mm
Distance between centers of first and second lid openings 1134 and 1136: 23.5 mm
The weight 1112 specification details are:
Outer diameter c: 50.0 mm
Diameter d of center bore 1130: 16.0 mm
Height e: 39.0 mm
The piston head 1118 specification details are
Diameter f: 59.7 mm
Height g: 16.5 mm
Outer holes 1214 (14 total) with a 9.65 mm diameter h, outer holes 1214 equally spaced with centers being 47.8 mm from the center of center hole 1218
Inner holes 1216 (7 total) with a 9.65 mm diameter i, inner holes 1216 equally spaced with centers being 26.7 mm from the center of center hole 1218
Center hole 1218 has a diameter j of ⅝ inches and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the support screen (not shown) on the ring stand 1040 above the receiving vessel 1024. Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of 12.5 mm±0.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery tube 1018 is dimensioned to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar (not shown). The constant hydrostatic head reservoir 1014 can be positioned on a laboratory jack 1016 in order to adjust its height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 3 g/sec for at least 10 minutes.

The piston/cylinder assembly 1028 is positioned on a 16 mesh rigid stainless steel support screen (not shown) (or equivalent) which is supported on a ring stand 1040 or suitable alternative rigid stand. This support screen (not shown) is sufficiently permeable so as to not impede salt solution 1032 flow and rigid enough to support the stainless steel mesh cloth (not shown) preventing stretching. The support screen (not shown) should be flat and level to avoid tilting the piston/cylinder assembly 1028 during the test. The salt solution 1032 passing through the support screen (not shown) is collected in a receiving vessel 1024, positioned below (but not supporting) the support screen (not shown). The receiving vessel 1024 is positioned on the balance 1026 which is accurate to at least 0.01 g. The digital output of the balance 1026 is connected to a computerized data acquisition system (not shown).

Preparation of Reagents (not Illustrated)

Figure 16:
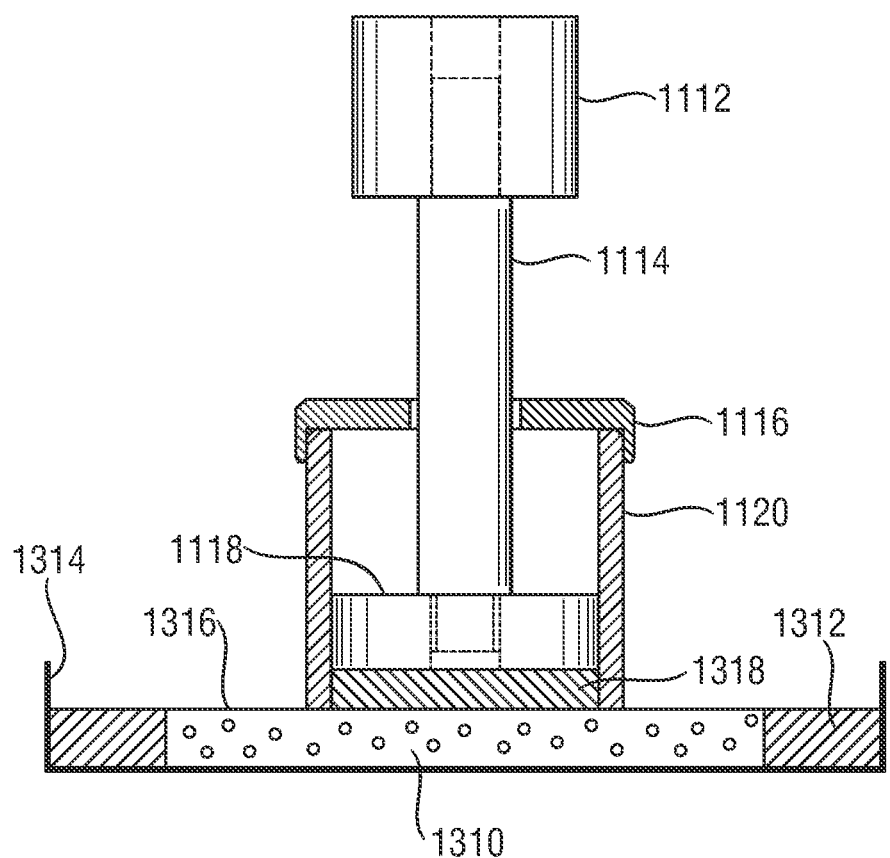
FIG. 16 is a cross-sectional side view of the piston/cylinder assembly of FIG. 14 placed on fritted disc for the swelling phase.

Jayco Synthetic Urine (JSU) 1312 (see FIG. 16) is used for a swelling phase (see UPM Procedure below) and 0.118 M Sodium Chloride (NaCl) Solution is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:

Potassium Chloride (KCl) 2.00 g
Sodium Sulfate ($Na_2SO4$) 2.00 g
Ammonium dihydrogen phosphate ($NH_4H_2PO_4$) 0.85 g
Ammonium phosphate, dibasic (($NH_4$)$_2HPO_4$) 0.15 g
Calcium Chloride ($CaCl_2$) 0.19 g—[or hydrated calcium chloride ($CaCl_2.2H_2O$) 0.25 g]
Magnesium chloride ($MgCl_2$) 0.23 g—[or hydrated magnesium chloride ($MgCl_2.6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask; and the flask is filled to volume with distilled water. A stir bar is added and the solution is mixed on a stirring plate until all the solids are dissolved.

Test Preparation

Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 1046. The piston/cylinder assembly 1028 without superabsorbent polymer particles is positioned under the caliper gauge (not shown) and a reading, $L_1$, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system (not shown). The ring stand 1040 with a 16 mesh rigid stainless steel support screen (not shown) is positioned above the receiving vessel 1024. The 16 mesh screen (not shown) should be sufficiently rigid to support the piston/cylinder assembly 1028 during the measurement. The support screen (not shown) must be flat and level.

UPM Procedure

The measurements should be preferably made on the superabsorbent polymer particles raw material before it is converted into an absorbent core. If this is not possible, a sufficient SAP sample should be obtained from the finished absorbent cores by manually extracting the SAP particles from the central layer.

The moisture content of the superabsorbent polymer particles is measured on a first sample according to the EDANA Moisture Content Test Method WSP 230.2.R3 (12) ("Superabsorbent materials—Polyacrylate superabsorbent powders—Moisture Content—weight loss upon heating"). Another sample of 1.5 g (±0.05 g) of superabsorbent polymer particles is weighed onto a suitable weighing paper or weighing aid using an analytical balance. If the moisture content of the superabsorbent polymer particles is greater than 5%, then the superabsorbent polymer particles weight should be corrected for moisture (i.e., in that particular case the added superabsorbent polymer particles should be 1.5 g on a dry-weight basis).

The empty cylinder 1120 is placed on a level benchtop 1046 and the superabsorbent polymer particles are quantitatively transferred into the cylinder 1120. The superabsorbent polymer particles are evenly dispersed on the screen (not shown) attached to the bottom 1148 of the cylinder 1120 by gently shaking, rotating, and/or tapping the cylinder 1120. It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The lid 1116 and piston shaft 1126 are then carefully rotated so as to align the third, fourth, fifth, and sixth linear index marks are then aligned. The piston head 1118 (via the piston shaft 1114) is then gently lowered to rest on the dry superabsorbent polymer particles. The weight 1112 is positioned on the upper portion 1128 of the piston shaft 1114 so that it rests on the shoulder 1124 such that the first and second linear index marks are aligned. Proper seating of the lid 1116 prevents binding and assures an even distribution of the weight on the hydrogel layer 1318.

Swelling Phase: An 8 cm diameter fritted disc (7 mm thick; e.g. Chemglass Inc. #CG 201-51, coarse porosity) 1310 is saturated by adding excess JSU 1312 to the fritted disc 1310 until the fritted disc 1310 is saturated. The saturated fritted disc 1310 is placed in a wide flat-bottomed Petri dish 1314 and JSU 1312 is added until it reaches the top surface 1316 of the fritted disc 1310. The JSU height must not exceed the height of the fitted disc 1310.

The screen (not shown) attached to the bottom 1148 of the cylinder 1120 is easily stretched. To prevent stretching, a sideways pressure is applied on the piston shaft 1114, just above the lid 1116, with the index finger while grasping the cylinder 1120 of the piston/cylinder assembly 1028. This "locks" the piston shaft 1114 in place against the lid 1116 so that the piston/cylinder assembly 1028 can be lifted without undue force being exerted on the screen (not shown).

The entire piston/cylinder assembly 1028 is lifted in this fashion and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fritted disc 1310. After a period of 60 minutes, the piston/cylinder assembly 1028 is removed from the fritted disc 1310, taking care to lock the piston shaft 1114 against the lid 1116 as described above and ensure the hydrogel layer 1318 does not lose JSU 1312 or take in air during this procedure. The piston/cylinder assembly 1028 is placed under the caliper gauge (not shown) and a reading, $L_2$, is recorded to the nearest 0.01 mm. If the reading changes with time, only the initial value is recorded. The thickness of the hydrogel layer 1318, $L_0$ is determined from $L_2-L_1$ to the nearest 0.1 mm.

The piston/cylinder assembly 1028 is transferred to the support screen (not shown) attached to the ring support stand 1040 taking care to lock the piston shaft 1114 in place against the lid 1116. The constant hydrostatic head reservoir 1014 is positioned such that the delivery tube 1018 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer (not shown) attached to the balance 1026, the quantity of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation. The flow rate $F_s$ (in g/s) is the slope of a linear least-squares fit to a graph of the weight of salt solution 1032 collected (in grams) as a function of time (in seconds) from 60 seconds to 600 seconds.

The Urine Permeability Measurement (Q) of the hydrogel layer 1318 is calculated using the following equation:

$$Q=[F_g \times L_0]/[\rho \times A \times \Delta P],$$

where $F_g$ is the flow rate in g/sec determined from regression analysis of the flow rate results, $L_0$ is the initial thickness of the hydrogel layer 1318 in cm, $\rho$ is the density of the salt solution 1032 in gm/cm³. A (from the equation above) is the area of the hydrogel layer 1318 in cm², $\Delta P$ is the hydrostatic pressure in dyne/cm², and the Urine Permeability Measurement, Q, is in units of cm³ sec/gm. The average of three determinations should be reported.

High Loft Nonwoven Layer Thickness and Density Measurement Method

This method is used to measure the thickness of a high loft fibrous nonwoven central layer in a standardized manner. The density can then be calculated from the thickness. Unless otherwise mentioned, the thickness and density are indicated for the high loft material in the absence of SAP particles. The measurement should preferably be made on the high loft material before it was converted into an absorbent core and thus free of SAP. If the starting material is not available, the high loft central layer can be obtained by carefully extracting it from an absorbent core, and removing the majority of SAP particles for example by careful shaking or suction. A freeze spray may be used to separate the central layer from the other layers. The samples should be kept at least 24 hours at 21° C.±2° C. and 50%±20% RH to equilibrate, in particular if they have been previously compressed.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 4.14 kPa of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The central layer is conditioned at least 24 hours as indicated above. Measurement procedure: The layer is laid flat with the bottom side, i.e. the side intended to be placed towards the backsheet in the finished article facing down. The point of measurement, i.e. the middle of the sample, is carefully drawn on the top side of the layer, taking care not to compress or deform the layer. In the unlikely case that the high loft nonwoven layer is not homogeneous in the transversal direction or longitudinal direction, the values are measured in the center of a sample corresponding to the center of an absorbent core that would be made from the sample. Typically however the high loft fibrous nonwoven layer is homogeneous.

The contact foot of the caliper gauge is raised and the central layer is placed flat on the base plate of the caliper gauge with the top side of the core up so that when lowered, the center of the foot is on the marked measuring point.

The foot is gently lowered onto the sample and released (ensure calibration to "0" prior to the start of the measurement). The caliper value is read to the nearest 0.01 mm, 10 seconds after the foot is released.

The procedure is repeated for each measuring point. Ten samples are measured in this manner for a given material and the average caliper is calculated and reported with an accuracy of one tenth mm. The basis weight of each sample is calculated by dividing the weight of each sample by their area.

The density, in g/cc, is calculated by dividing the basis weight (in g/cm²) of the material by the thickness (in cm).

Misc.

Dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for use in an absorbent article, the absorbent core extending in a transversal direction and a longitudinal direction, the absorbent core comprising:
    a fluid-permeable top layer;
    a bottom layer;
    a central layer sandwiched between the top layer and the bottom layer, the central layer having a front edge, a back edge and two longitudinally extending side edges, wherein the central layer is a high loft fibrous nonwoven layer comprising synthetic fibers defining void spaces therebetween; and
    superabsorbent polymer particles disposed within the high loft nonwoven layer in the void spaces between the synthetic fibers of a first zone of the central layer;
    wherein the central layer has a density of about 0.200 g/cc or less at a pressure of 4.14 kPa,
    wherein a second zone of the central layer comprises a longitudinally-extending channel substantially free of superabsorbent polymer particles, and
    wherein the first zone and the second zone both comprise the high loft fibrous non-woven layer.

2. The absorbent core of claim 1, wherein at least one of the top layer, the bottom layer, and the central layer comprises a carded nonwoven.

3. The absorbent core of claim 1, wherein the superabsorbent polymer particles have a UPM of about $30 \times 10^{-7}$ cm$^3$·s/g or less.

4. The absorbent core of claim 1, wherein at least one of the top layer and the bottom layer is attached to the central layer by gluing.

5. The absorbent core of claim 1, wherein at least one of the top layer and the bottom layer are bonded to the central layer in the channels by at least one of gluing, mechanical bonding, ultrasonic bonding, pressure bonding, and heat bonding.

6. The absorbent core of claim 1, wherein the channel is spaced away from the longitudinally extending side edges of the core.

7. The absorbent core of claim 1, comprising a nonwoven wrapping layer configured to wrap at least one of the top layer, the bottom layer, and the central layer.

8. The absorbent core of claim 7, wherein the wrapping layer completely covers one of the bottom layer or the top layer and forms a C-wrap around the longitudinally extending side edges of the central layer to at least partially cover the other of the top layer or the bottom layer.

9. The absorbent core of claim 1, wherein the channel is completely surrounded by at least one zone of the central layer comprising superabsorbent polymer particles.

10. The absorbent core of claim 1, wherein the channel extends longitudinally from the front edge to the back edge of the central layer.

11. The absorbent core of claim 1, comprising a least a pair of channels symmetrically disposed along a longitudinal axis of the core.

12. The absorbent core of claim 11, wherein the channels are curved.

13. The absorbent core of claim 1, wherein the central layer is a spunlaid nonwoven of synthetic fibers and is free of cellulose fibers.

14. The absorbent core of claim 1, comprising a first central layer and a second central layer between the top layer and the bottom layer, wherein at least one of the first central layer and the second central layer is a central layer according to claim 1.

15. The absorbent core of claim 1, wherein the longitudinally-extending channel extends across the entire central layer from the front edge to the back edge.

16. An absorbent article, the absorbent article comprising:
    a liquid management layer; and
    an absorbent core extending in a transversal direction and a longitudinal direction, the absorbent core comprising:
        a fluid-permeable top layer;
        a bottom layer;
        a central layer sandwiched between the top layer and the bottom layer, the central layer having a front edge, a back edge and two longitudinally extending side edges, wherein the central layer is a high loft fibrous nonwoven layer comprising synthetic fibers defining void spaces therebetween; and
        superabsorbent polymer particles disposed within the high loft nonwoven layer in the void spaces between the synthetic fibers of a first zone of the central layer,
        wherein the central layer has a density of about 0.200 g/cc or less,
        wherein a second zone of the central layer comprises a longitudinally-extending channel substantially free of superabsorbent polymer particles, and
        wherein the first zone and the second zone both comprise the high loft fibrous non-woven layer.

17. The absorbent article of claim 16, comprising a topsheet and a backsheet.

18. The absorbent article of claim 17, wherein the liquid management layer is positioned between the absorbent core and topsheet.

19. The absorbent article of claim 16, wherein the synthetic fibers comprise at least one of polypropylene fibers, polyamide fibers, and polyethylene terephthalate fibers.

20. The absorbent article of claim 16, wherein the central layer comprises a spunmelt nonwoven.

* * * * *